United States Patent

Klose et al.

[11] Patent Number: 5,998,453
[45] Date of Patent: Dec. 7, 1999

[54] OXAZOLIDINONE COMPOUNDS AND PHARMACEUTICAL PREPARATION CONTAINING THEM

[75] Inventors: Walter Klose; Gerald Kirsch; Andreas Huth; Wolfgang Froehlich; Henry Laurent, all of Berlin, Germany

[73] Assignee: Schering Aktiengesellschaft, Berlin, Germany

[21] Appl. No.: 08/467,885

[22] Filed: Jun. 6, 1995

Related U.S. Application Data

[63] Continuation of application No. 08/504,719, Nov. 17, 1994, Pat. No. 5,783,591, which is a continuation of application No. 08/119,804, Sep. 13, 1993, abandoned, which is a continuation of application No. 07/977,972, Nov. 18, 1992, abandoned, which is a continuation of application No. 07/854,788, Mar. 23, 1992, abandoned, which is a continuation of application No. 06/887,763, which is a continuation of application No. PCT/DE85/00472, Oct. 19, 1984, abandoned.

[30] Foreign Application Priority Data

Oct. 19, 1984 [DE] Germany .............................. 34 38 839

[51] Int. Cl.⁶ .................... C07D 263/24; A61K 31/42
[52] U.S. Cl. ............................................ 514/376; 548/232
[58] Field of Search .......................... 514/376; 548/228, 548/232

[56] References Cited

U.S. PATENT DOCUMENTS

| 4,012,495 | 3/1977 | Schmiechen et al. |
|---|---|---|
| 4,186,129 | 1/1980 | Huth et al. .............................. 548/232 |
| 4,208,406 | 6/1980 | Lapinet et al. ............................. 536/27 |
| 4,824,838 | 4/1989 | Wachtel et al. .......................... 548/232 |

FOREIGN PATENT DOCUMENTS

| 3438839 | 4/1986 | Germany . |
|---|---|---|
| 3639225 | 5/1988 | Germany . |
| 86-02268 | 4/1986 | WIPO . |

OTHER PUBLICATIONS

Schneider et al. Chem. Abstr, vol. 122 Entry 1–51229 (1995).
Schmiechen et al. Chem. Abstr vol. 113 Entry 145263 (1990).
Wachtel et al. Chem. Abstr vol. 109 Entry 86345 (1988) Abstracting DE 3639 225.

*Primary Examiner*—John M. Ford
*Attorney, Agent, or Firm*—Millen, White, Zelano & Branigan, P.C.

[57] ABSTRACT

Pharmaceutical preparations for the local treatment of inflammations are claimed herein, characterized in that they contain as the active ingredient one or two compounds of general Formula I

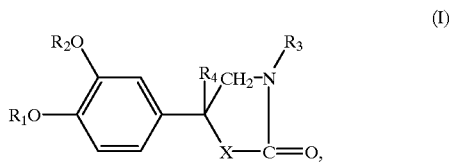

wherein X is an oxygen atom or a methylene group, $R_1$ and $R_2$ represent a hydrogen atom or a hydrocarbon residue of maximally eight carbon atoms, optionally interrupted by an oxygen atom, $R_3$ is a hydrogen atom or a hydrocarbon residue of maximally eight carbon atoms, optionally substituted by an oxo group, and $R_4$ is a hydrogen atom or an alkyl group of maximally four carbon atoms.

14 Claims, No Drawings

OXAZOLIDINONE COMPOUNDS AND PHARMACEUTICAL PREPARATION CONTAINING THEM

This is a continuation of the application Ser. No. 08/504,719, filed Nov. 17, 1994 (now U.S. Pat. No. 5,783,591, issued Jul. 21, 1998), which is a continuation of Ser. No. 08/119,804, filed Sep. 13, 1993 (now abandoned), which is a continuation of Ser. No. 07/977,972, filed Nov. 18, 1992 (now abandoned), which is a continuation of Ser. No. 07/854,788, filed Mar. 23, 1992 (now abandoned), which is a continuation of Ser. No. 06/887,763 filed Mar. 16, 1988, (now abandoned), which is a National Phase PCT application of DE 85/00472, filed Oct. 19, 1884.

The invention relates to the subject matter characterized in the claims.

Numerous compounds of general Formula I according to claim 1 have been known heretofore. Thus, U.S. Pat. No. 4,012,495, for example, describes pyrrolidone derivatives of general Formula I, and U.S. Pat. No. 4,186,129 discloses oxazolidinone derivatives of general Formula I. It can be seen from these patents that these compounds are distinguished by centrally depressive, antidopaminergic, antinociceptive, and anticonvulsive effectiveness and moreover exhibit strong phosphodiesterase-inhibiting properties.

It has now been found that the compounds of general Formula I according to claim 1 exhibit, upon topical application, a strong anti-inflammatory activity.

Compounds of general Formula I according to claim 1 which have anti-inflammatory activity are those carrying as substituents $R_1$ and $R_2$ a hydrogen atom or a hydrocarbon residue of maximally eight carbon atoms, optionally interrupted by an oxygen atom. The substituents $R_1$ and $R_2$ can be identical or different. Suitable hydrocarbon residues $R_1$ and $R_2$ are saturated or unsaturated, alicyclic, cycloaliphatic or aromatic hydrocarbon residues, such as, for example, the methyl group, the ethyl group, the propyl group, the isopropyl group, the butyl group, the sec-butyl group, the isobutyl group, the tert-butyl group, the pentyl group, the hexyl group, the allyl group, the 2-propynyl group, the cyclopentyl group, the cyclohexyl group, the cyclopropylmethyl group, the cyclopentylmethyl group, the cyclopentenylmethyl group, the phenyl group, or the benzyl group.

Suitable hydrocarbon residues $R_1$ and $R_2$, interrupted by an oxygen atom, are, for example, the 2-tetrahydrofuranyl group and the 2-tetrahydropyranyl group. Especially suitable as the substituent $R_1$ is the methyl residue. The compounds of general Formula I according to claim 1 can contain, as hydrocarbon residues $R_3$, the same groups as recited for substituents $R_1$ and $R_2$. Suitable hydrocarbon residues substituted by an oxo group are, in particular, hydrocarbon residues substituted in the α-position, i.e. acyl groups. Suitable acyl groups are those derived from saturated or unsaturated, aliphatic, cycloaliphatic, or aromatic hydrocarbons of maximally eight carbon atoms, such as, for example, 1-oxoalkyl groups (formyl, acetyl, propionyl, butyryl, isobutyryl, trimethylacetyl groups, etc.); 1-oxoalkylcycloalkyl groups such as the cyclopentylcarbonyl group, the cyclohexylcarbonyl group, or the 3-cyclopropyl-1-oxopropyl group; or aromatic acyl groups, such as the benzyl group or 4-methylbenzyl group.

Suitable alkyl groups $R_4$ are, for example, the ethyl group, the propyl group, the isopropyl group, or especially the methyl group.

Previously unknown compounds of general Formula I according to claim 1 are the oxazolidinone derivatives of general Formula Ia characterized in claim 4. These compounds can be prepared in the same way as the previously known oxazolidinone derivatives, by converting an acetophenone of general Formula II

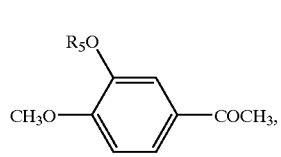
(II)

wherein $R_5$ is a 2 to 4 carbon atom hydrocarbon residue—therefor into a cyanohydrin of general Formula III

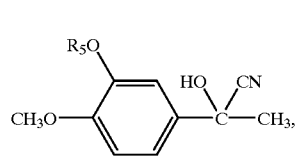
(III)

reducing the latter to an amine of Formula IV

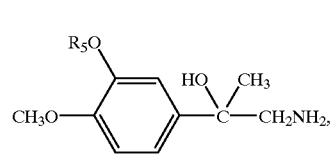
(IV)

and condensing this compound with a carbonyl compound of general Formula V

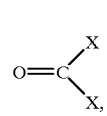
(V)

wherein X means respectively chlorine atoms, lower alkoxy groups (preferably methoxy groups or ethoxy groups) or 1-imidazolyl residues. This reaction sequence can be performed, for example, under the conditions described in U.S. Pat. No. 4,186,129.

The anti-inflammatory efficacy of the compounds of general Formula I according to claim 1 was determined by means of the rat ear test according to Tonelli (Endocrinol. 77: 625 [1965], and Proc. Soc. Exp. Med. 159: 223 [1978]) as follows:

Varying concentrations of test compound were dissolved in a croton oil solution which was 5 vol-% ethanolic or were dispersed by a five-minute treatment in an ultrasonic bath. Respectively 50 μl per concentration of this solution and compound-free croton oil solution were applied by means of a 1 ml tuberculin syringe to the two external ear surfaces of 10 anesthetized Wistar rats (weighing 160–200 g). An untreated group served as control.

Five hours after treatment, the animals were sacrificed by treatment with gaseous $CO_2$, the ears were cut off and weighed in pairs.

The percentage inhibition of the weight increase caused by croton oil was determined in each case as a measure for the topical anti-inflammatory activity of the test compounds.

The tables set forth below show the results obtained in this test.

TABLE 1

| No. | Compound | $ED_{50}$ [mg/kg] |
|---|---|---|
| 1 | Bufexamac | 15.0 |
| 2 | Bendazac | 15.0 |
| 3 | Hydrocortisone 17-butyrate | 0.5 |
| 4 | 4-(3-Cyclopentyloxy-4-methoxy-phenyl)-2-pyrrolidone | 0.6 |
| 5 | 4-[4-Methoxy-3-(3-tetrahydrofuryl-oxy)phenyl]-2-pyrrolidone | 0.2 |
| 6 | 4-(3-Isobutoxy-4-nmethoxyphenyl)-2-pyrrolidone | 1.1 |
| 7 | 5-Methyl-5-[4-methoxy-3-(3-tetra-hydropyranyloxy)phenyl]-oxazolidinone | 0.18 |
| 8 | 5-(3-Cyclopropylmethoxy-4-methoxy-phenyl)-3,5-dimethyl-2-oxazolidinone | 0.22 |
| 9 | 5-(3-Ethoxy-4-methoxyphenyl)-3,5-dimethyl-2-oxazolidinonen | 0.18 |
| 10 | 5-(3-Propynyloxy-4-methoxyphenyl)-2-oxazolidinone | 2.0 |
| 11 | 5-(3,4-Dimethoxyphenyl)-5-methyl-2-oxazolidinone | 0.6 |
| 12 | 5-(3-Cyclopentyloxy-4-methoxy-phenyl)-2-oxazolidinone | 1.0 |
| 13 | 5-(3-Cyclopentyloxy-4-methoxy-phenyl)-5-methyl-2-oxazolidinone | 1.2 |
| 14 | 5-[3-(3-Tetrahydrofuryloxy)-4-methoxyphenyl]-2-oxazolidinone | 0.5 |
| 15 | 5-(4-Methoxy-3-propoxyphenyl)-2-oxazolidinone | 1.3 |
| 16 | 5-(3-Allyloxy-4-methoxyphenyl)-2-oxazolidinone | 3.2 |
| 17 | 5-Methyl-5-(3-cyclopropylmethoxy-4-methoxyphenyl)-2-oxazolidinone | 0.5 |
| 18 | 5-Methyl-5-(4-methoxy-3-propoxy-phenyl)-2-oxazolidinone | 2.3 |
| 19 | 5-Methyl-5-(3-butoxy-4-methoxy-phenyl)-2-oxazolidinone | 2.7 |
| 20 | 5-Methyl-5-(3-isopropoxy-4-methoxyphenyl -2-oxazolidinone | 1.7 |
| 21 | 5-Methyl-5-(3-ethoxy-4-methoxy-phenyl)-2-oxazolidinone | 1.3 |

The results thus compiled show that the compounds of general Formula I upon topical application are substantially more effective as anti-inflammatory agents than the previously known, comparable compounds 1 and 2. They attain almost the intensity of effectiveness of highly efficacious corticoids, such as, for example, hydrocortisone 17-butyrate (compound 3).

The medical specialties are produced in the usual way by converting the active agents with suitable additives into the desired form of application, such as, for example, solutions, lotions, ointments, creams, or plasters. In the thus-formulated medicines, the active agent concentration is dependent on the form of application. In case of lotions, creams, and ointments, an active agent concentration of 0.01% to 10% is employed with preference.

The lotions or creams (oil/water emulsions) and the ointments (water/oil emulsions) can be conventionally manufactured with the use of conventional emulsifiers (Kirk Othmer: Encyclopedia of Chemical Technology, 3rd edition, 1979, John Wiley and Sons, New York, etc., vol. 8: 900–930; and Dr. Otto-Albrecht Neumüller: Römpps Chemie Lexikon, 7th edition, 1973, Franck'sche Verlagshandlung Stuttgart, pages 1009–1013). The waxes, emulsifiersand other additives utilized for these emulsions are the same as conventionally employed (Dr. Otto-Albrecht Neumüller: Römpps Chemie Lexikon, 7th edition, 1973, Franck'sche Verlagshandlung Stuttgart, pages 1427 and 1428).

A pharmaceutical preparation according to this invention in the form of an oil/water emulsion can consist of hydrophilic and/or lipophilic active agents, a fat phase, an oil/water emulsifier, an aqueous phase, and a preservative.

Suitable hydrophilic and/or lipophilic active agents are moisturizing factors (hydrocomplexes), e.g. glycerol, polyethylene glycols or amino acid mixtures, "Puroba" oil (=jojoba oil), vitamins (preferably vitamins A and E), vitalizing complexes (such as, for example, placenta extracts), enzymes, herbal extracts (e.g. Hanamelis extract or camomile extract), or proteins (such as, for example, collagen). Hydrocarbons, e.g. "Vaseline", paraffins, or stearin, or waxes, e.g. beeswax, are suitable as the oily phase or lipid phase in the oil/water emulsion. Suitable oil/water emulsifiers are, for example, stearyl alcohol, polyoxyethylene stearates (e.g. "MYRJ"), complex emulsifiers (such as, for example, "Amphoterin"), and sorbitan fatty acid esters (e.g. "Span"), or carboxyvinyl polymers (e.g. "Carbopol"). The aqueous phase can additionally contain buffer compounds, such as, for example, the disodium salt of ethylenediamine-N,N,N',N'-tetraacetic acid and preservatives, such as chlorquinaldol, "Parabens", or benzalkonium chloride.

In the oil/water emulsion, the proportion of internal emulsion is preferably 10–49% by weight; the particle size of the internal emulsion ranges preferably between 1 μm and 100 μm.

A pharmaceutical preparation according to this invention in the form of a water/oil emulsion likewise consists of hydrophilic and/or lipophilic active agents, as they are also employed in the oil/water emulsion, a lipid phase, a water/oil emulsifier, and an aqueous phase. Hydrocarbons can be utilized as the oily phase or lipid phase of the water/oil emulsion, e.g. paraffins and "Vaseline", synthetic, vegetable and animal oils or waxes (such as, for example, olive oil, peanut oil, fine bone oil, almond oil, lanolin, beeswax, or sunflower oil);as the aqueous phase, purified, demineralized water; and as the water/oil emulsifier, wool fat (=lanolin), fatty alcohols, e.g. cetyl alcohol, myristyl alcohol, stearyl alcohol, or ceryl alcohol, fatty acid esters, such as, for example, beeswax (cera alba), or wax alcohol esters or mixed esters (such as, for example, "Dehymuls").

In the water/oil emulsion, the proportion of internal emulsion is preferably 30–49% by weight, the particle size of the internal emulsion ranging preferably between 1 μm and 100 μm.

The finely disperse system is additionally combined with the micronized active agent (particle size preferably 1–20 μm) and optionally also with fragrance media, e.g. those of the "Crematest" series, and stirred until uniform distribution results.

The compounds of general Formula I according to claim 1 are moreover suitable, optionally in combination with the customary excipients and auxiliary agents, also for the manufacture of inhalants that can be used for therapy of allergic diseases of the respiratory tract, e.g. bronchial asthma or rhinitis.

The compounds of Formula I are furthermore suitable, also in the form of capsules, tablets or dragees preferably containing 10–200 mg of active ingredient and being administered orally, or in the form of suspensions containing preferably 100–1,500 mg of active agent per dosage unit and being administered rectally, likewise for the treatment of allergic diseases of the intestinal tract, such as colitis ulcerosa and colitis granulomatosa.

The examples set forth below serve for explaining the invention.

1. EMBODIMENTS CONCERNING PHARMACEUTICAL PREPARATIONS

EXAMPLE 1

(a) Preparation of Oil/Water Emulsion 10.00 g of disodium edetate and 10.00 g of chlorquinaldol are dissolved in 300.00 g of purified, demineralized water and combined with 10.00 g of "Carbopol".

This mixture is introduced under vigorous agitation into a melt of 80.00 g of "Vaseline" (DAB 8)—DAB being the abbreviation for the German Pharmacopoeia, official edition, 8th printing, 1978—40.00 g of stearyl alcohol, 30.00 g of "MYRJ" and 50.00 g of jojoba oil. The mixture is stirred further until an emulsion is produced having a particle size of 20–70 μm.

(b) Production of Water/Oil Emulsion 230.00 g of purified, demineralized water is introduced under vigorous agitation into a melt of 220.00 g of "Vaseline" (DAB 8), 10.00 g of "Dehymuls", and 10.00 of cera alba. The mixture is further stirred until an emulsion is formed having a particle size of 20–70 μm.

(c) Production of a Cream

The water/oil emulsion is introduced under vigorous agitation into the oil/water emulsion under a vacuum of 10 torr. Stirring is continued until a dispersion is produced having a particle size of 10–50 μm, and the vacuum is removed.

Under agitation, 95.000 g of this ointment base is combined with 5.000 g of 5-(3,4-dimethoxyphenyl)-5-methyl-3-oxazolidinone—micronized; particle size predominantly 1–20 μm—and stirring is continued until the active ingredient has been uniformly distributed in the ointment base.

EXAMPLE 2

97.000 g of the ointment base produced according to Example 1(c) is combined with 3.000 g of 4-(3-cyclopentyloxy-4-methoxyphenyl)-2-pyrrolidone—micronized; particle size predominantly 1–20 μm—and the mixture is stirred until the active agent has been uniformly distributed in the ointment base.

EXAMPLE 3

95.000 g of the ointment base prepared in accordance with Example 1(c) is combined with 5.000 g of 4-(3-isobutoxy-4-methoxyphenyl)-2-pyrrolidone—micronized; particle size primarily 1–20 μm—and the mixture is agitated until the active ingredient has been uniformly distributed in the ointment base.

EXAMPLE 4

97.500 g of the ointment base produced according to Example 1(c) is mixed with 2.500 g of 5-[4-methoxy-3-(2-tetrahydrofuranyloxy)phenyl]-2-oxazolidinone—micronized; particle size predominantly 1–20 μm—and the mixture is agitated until the active ingredient has been uniformly distributed in the ointment base.

EXAMPLE 5

95.000 g of the ointment base prepared in Example 1(c) is combined with 5.000 g of 5-methyl-5-(3-cyclopropylmethoxy-4-methoxyphenyl)-2-oxazolidinone—micronized; particle size predominantly 1–20 μm—and the mixture is agitated until the active agent has been uniformly distributed in the ointment base.

EXAMPLE 6

45.000 g of "Vaseline" (DAB 8), 19.600 g of paraffin oil, 5.000 g of cetyl alcohol, 5.000 g of beeswax, and 5.000 g of sorbitan sesquioleate are made into a melt, combined with a solution of 0.2000 g of p-hydroxybenzoic acid ester in 15.2 g of demineralized water, and emulsified at 50° C. The emulsion is then allowed to cool, combined with 5.000 g of 4-(3-cyclopentyloxy-4-methoxyphenyl)-2-pyrrolidone—micronized; particle size predominantly 1–20 μm—and the mixture is agitated until the active agent has been uniformly distributed in the ointment base.

EXAMPLE 7

A mixture is prepared from 1.000 g of micronized 4-(3-cyclopentyloxy-4-methoxyphenyl)-2-pyrrolidone (average particle size: smaller than 8 μm) and 39.000 g of ground lactose. Respectively 200 mg of the mixture is utilized for applying the inhalant.

EXAMPLE 8

A spray can equipped with a metering valve (one dose= 200 mg; this corresponds to 5 mg of active agent) is filled with 250 mg of 4-(3-cyclopentyloxy-4-methoxyphenyl)-2-pyrrolidone and 5.0 ml of "Freon" 12/114 (40:60).

EXAMPLE 9

5.00 g of polyoxyethylene-polyoxypropylene polymer and 25.00 g of polyvinylpyrrolidone are dissolved in 800 ml of twice-distilled water; the solution is combined with 50.000 g of 4-(3-cyclopentyloxy-4-methoxyphenyl)-2-pyrrolidone and homogenized. The resultant suspension is then filled up to 2,000 ml with twice-distilled water. Respectively 50 ml of the suspension is introduced into a small infusion bottle, the samples are frozen at −30° C. for 150 minutes and freeze-dried for 48 hours.

Prior to use, the sample is resuspended in 50 ml of twice-distilled water, and this suspension is administered rectally.

2. EMBODIMENTS CONCERNING THE SYNTHESIS OF THE OXAZOLIDINONE DERIVATIVES OF GENERAL FORMULA II

EXAMPLE 1

Under argon, 3.10 g (15.0 millimoles) of 3-allyloxy-4-methoxyacetophenone, 2.18 ml (16.4 mmol) of trimethylsilyl cyanide and 126 mg (0.39 mmol) of zinc iodide were stirred for 5 hours at 100° C. and for 14 hours at room temperature. The reaction mixture was combined with 4.6 ml of ether and added dropwise to 0.69 g (18.5 mmol) of lithium aluminum hydride in 13.5 ml of ether. After an agitation period of one hour at a bath temperature of 40° C., the reaction mixture was decomposed in succession with 0.7 ml of water, 0.75 ml of 4N sodium hydroxide solution, and with 2.1 ml of water. The thus-formed solid was washed out several times with ether, the combined ether phases were dried over sodium sulfate, filtered, and concentrated (3.33 g of oil). After another addition of 42 mg of zinc iodide and 0.73 ml of trimethylsilyl cyanide, the mixture was stirred for another 4 hours at 100° C. The reaction mixture was diluted with 3 ml of ether and added dropwise to a suspension of 240 mg of lithium aluminum hydride in 6 ml of ether. Subsequently the mixture was stirred at 40° C. for 30 minutes and thereafter decomposed with 0.2 ml of water, 0.26 ml of 4N sodium hydroxide solution, and 0.8 ml of water. The thus-formed solid was repeatedly washed with ether; the combined ether phases were dried over sodium sulfate, filtered, and concentrated. The oily residue (2.06 g) was stirred in 31 ml of tetrahydrofuran with 2.11 g (12.4 mmol) of carbonyldiimidazole for 20 hours at room temperature. The reaction mixture was concentrated under vacuum, the residue was dissolved in ethyl acetate, the organic solution was washed with 2N hydrochloric acid and water, dried over sodium sulfate, filtered, and concentrated (1.52 g of an oil). Chromatography on silica gel with methylene chloride/ether (1:1) yielded 260 mg of 5-methyl-5-(3-allyloxy-4-methoxyphenyl)-2-oxazolidinone as an oil.

$^1$H-NMR (CDCl$_3$): δ=1.75 (s, 2H), 3.63 (s, 2H), 3.83 (s, 3H), 4.55 (pseudo d, 2H), 5.10–6.23 (m, 4H), 6.80 (pseudo d, 3H)

EXAMPLE 2

2.84 g (12.9 mmol) of 3-cyclopropylmethoxy-4-methoxyacetophenone, 1.87 ml (14.0 mmol) of trimethylsilyl cyanide, and 109 mg (0.33 mmol) of zinc iodide were stirred for 5 hours at 100° C. and for 14 hours at room temperature. After adding 4.5 ml of ether, the mixture was added dropwise to 0.6 g (15.8 mmol) of lithium aluminum hydride in 12 ml of ether and stirred for one hour at 40° C. (bath temperature). The reaction mixture was combined in succession with 0.7 ml of water, 0.75 ml of 4N sodium hydroxide solution and 2.1 ml of water. The thus-formed solid was repeatedly washed with ether, the combined ether phases were dried with sodium sulfate, filtered, and concentrated under vacuum. The residue (2.31 g of an oil) was stirred with 2.21 g (13.0 mmol) of carbonyldiimidazole in 33 ml of tetrahydrofuran at room temperature for 4 hours. The procedure was continued analogously to Example 1. Yield: 558 mg of 5-methyl-5-(3-cyclopropylmethoxy-4-methoxyphenyl)-2-oxazolidinone, mp 96–97° C.

EXAMPLE 3

1.63 g (7.8 mmol) of 3-propoxy-4-methoxyacetophenone, 1.1 ml (8.5 mmol) of trimethylsilyl cyanide, and 66 mg (0.21 mmol) of zinc iodide were agitated for 4.5 hours at 100° C. and for 14 hours at room temperature. The reaction mixture was combined with 4.6 ml of ether and added dropwise to 0.36 g (9.6 mmol) of lithium aluminum hydride in 7 ml of ether. After one hour of agitation at 40° C. (bath temperature), the reaction mixture was decomposed in succession with 0.4 ml of water, 0.4 ml of 4N sodium hydroxide solution, and 1 ml of water. Further procedure analogous to Example 1, but in the repeated addition of reagents, 20 mg of zinc iodide and 0.36 ml of trimethysilyl cyanide were utilized, and the mixture was decomposed with 0.1 ml of water, 0.13 ml of 4N sodium hydroxide solution, and 0.4 ml of water. For carbonylation, 1.19 g (7.0 mmol) of carbonyldiimidazole in 17.5 ml of tetrahydrofuran was utilized, thus obtaining 152 mg of 5-methyl-5-(4-methoxy-3-propoxyphenyl)-2-oxazolidinone as a crystalline oil. Recrystallization from ethyl acetate produced a melting point of 78° C.

EXAMPLE 4

3.47 g (15.6 mmol) of 3-butoxy-4-methoxyacetophenone, 2.26 ml (17.0 mmol) of trimethylsilyl cyanide, and 131 mg (0.91 mmol) of zinc iodide were stirred for 5 hours at 100° C. and for 14 hours at room temperature. After adding 4.6 ml of ether, the mixture was added dropwise to 0.73 g (19.2 mmol) of lithium aluminum hydride in 14 ml of ether and agitated for one hour at 40° C. (bath temperature). The procedure was continued analogously to Example 2, but using 2.18 g (12.8 mmol) of carbonyldiimidazole in 32.5 ml of tetrahydrofuran, thus obtaining 569 mg of 5-methyl-5-(3-butoxy-4-methoxyphenyl)-2-oxazolidinone, mp 108–109° C. (from ethyl acetate).

EXAMPLE 5

3.01 g (14.5 mmol) of 3-isopropyl-4-methoxyacetophenone, 2.1 ml (15.8 mmol) of trimethylsilyl cyanide, and 122 mg (0.38 mmol) of zinc iodide were stirred under argon for 5 hours at 100° C. and for 14 hours at room temperature. The further procedure took place analogously to Example 1, yielding 456 mg of 5-methyl-5-(3-isopropoxy-4-methoxyphenyl)-2-oxazolidinone, mp 67–69.5° C.

EXAMPLE 6

Under argon, 1.66 g (8.55 mmol) of 3-ethoxy-4-methoxyacetophenone was agitated with 1.24 ml (9.3 mmol) of trimethylsilyl cyanide and 72 mg (0.22 mmol) of zinc iodide for 5 hours at 100° C. and for 14 hours at room temperature. The reaction mixture was diluted with 2.5 ml of ether and added dropwise to 0.4 g (10.5 mmol) of lithium aluminum hydride in 8 ml of ether. After a stirring period of one hour at 40° C. (bath temperature), the reaction mixture was decomposed in succession with 0.45 ml of water, 0.45 ml of 4N sodium hydroxide solution and 1.1 ml of water. The thus-formed solid was repeatedly washed out with ether, and the combined ether phases were dried over sodium sulfate, filtered, and concentrated under vacuum. The residue (1.5 g) was stirred in 24 ml of tetrahydrofuran with 1.61 g (9.5 mmol) of carbonyldiimidazole for 4 hours at room temperature. The reaction solution was concentrated, the residue was dissolved in ethyl acetate, the organic solution was washed with 2N hydrochloric acid and water, dried over sodium sulfate, filtered, and concentrated (0.8 g of an oil). Chromatography on silica gel with methylene chloride/ether (1:1) yielded 370 mg of 5-methyl-5-(3-ethoxy-4-methoxyphenyl)-2-oxazolidinone, mp 63–65° C.

EXAMPLE 7

Under argon, 3.7 g (15.7 mmol) of 4-methoxy-3-(3-tetrahydrofuryloxy-acetophenone, 2.3 ml (17.1 mmol) of trimethylsilyl cyanide, and 134 mg (0.40 mmol) of zinc iodide were stirred for 5 hours at 100° C. and for 14 hours at room temperature. The process was continued analogously to Example 1, thus obtaining 600 mg of 5-methyl-5-[4-methoxy-3-(3-tetrahydrofuryloxy)phenyl]-2-oxazolidinone as a colorless oil.

EXAMPLE 8

500 mg (1.8 mmol) of 5-methyl-5-(3-cyclopropylmethoxy-4-methoxyphenyl)-2-oxazolidinone, 113 mg (2.0 mmol) of potassium hydroxide, and 0.15 ml (2.2 mmol) of methyl iodide were stirred in 4 ml of tetrahydrofuran for 4 hours at room temperature. The reaction mixture was filtered, the filtrate combined with 30 ml of water and then extracted with ethyl acetate. The ethyl acetate phase was washed with water, dried over sodium sulfate, filtered, and concentrated (390 mg of a yellow oil). By PSC separation with methylene chloride/ether (1:1), 212 mg of 5-(3-cyclopropylmethoxy-4-methoxyphenyl)-3,5-dimethyl-2-oxazolidinone was obtained as an oil.

EXAMPLE 9

500 mg (2.0 mmol) of 5-methyl-5-(3-ethoxy-4-methoxyphenyl)-2-oxazolidinone, 125 mg (2.22 mmol) of potassium hydroxide, and 0.167 ml (2.38 mmol) of methyl iodide were stirred in 4 ml of tetrahydrofuran for 4 hours at room temperature. The process was continued analogously to Example 8, thus obtaining 201 mg of 5-(3-ethoxy-4-methoxyphenyl)-3,5-dimethyl-2-oxazolidinone as an oil.

EXAMPLE 10

500 mg (2.0 mmol) of 5-methyl-5-(3-ethoxy-4-methoxyphenyl)-2-oxazolidinone was first stirred with 60 mg (2.5 mmol) of sodium hydride in 14 ml of dimethylformamide for 30 minutes and, after addition of 0.26 ml (3.0 mmol) of (bromomethyl)cyclopropane for 17 hours at room temperature. The reaction mixture was combined with 50 ml of water and then extracted with ethyl acetate. The ethyl acetate phase was washed with water, dried over sodium sulfate, filtered, and concentrated (766 mg of a yellow oil). Chromatography on silica gel with methylene chloride/ether (1:1) yielded 438 mg of 5-methyl-5-(3-ethoxy-4-methoxyphenyl)-3-cyclopropylmethyl-2-oxazolidinone as an oil.

EXAMPLE 11

500 mg (1.8 mmol) of 5-methyl-5-(3-cyclopropylmethoxy-4-methoxyphenyl)-2-oxazolidinone was first stirred with 75 mg (3.1 mmol) of sodium hydride in 17 ml of dimethylformamide for 30 minutes and, after adding 0.25 ml (2.7 mmol) of isopropyl bromide, for 17 hours at room temperature. The process was continued analogously to Example 1, thus obtaining 169 mg of 5-methyl-5-(3-cyclopropylmethoxy-4-methoxyphenyl)-3-isopropyl-2-oxazolidinone as an oil.

EXAMPLE 12

500 mg (1.8 mmol) of 5-methyl-5-(3-cyclopropylmethoxy-4-methoxyphenyl)-2-oxazolidinone was first agitated with 75 mg (3.1 mmol) of sodium hydride in 17 ml of dimethylformamide for 30 minutes and, after adding 0.32 ml (2.7 mmol) of benzyl bromide,for 2 hours at room temperature. The procedure was continued analogously to Example 10, thus obtaining 348 mg of 5-methyl-5-(3-cyclopropylmethoxy-4-methoxyphenyl)-3-benzyl-2-oxazolidinone as an oil.

We claim:
1. An oxazolidinone compound of Formula Ia

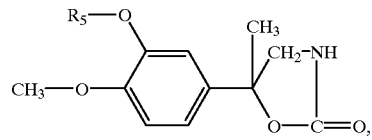

wherein $R_5$ is a hydrocarbon of two to four carbon atoms.
2. A compound according to claim 1, wherein $R_5$ is ethyl, propyl, isopropyl, butyl, isobutyl, tert-butyl, allyl, 2-propynyl or cyclopropylmethyl.
3. 5-methyl-5-(3-allyloxy-4-methoxyphenyl)-2-oxazolidinone, a compound of claim 1.
4. 5-methyl-5-(3-cyclopropylmethoxy-4-methoxyphenyl)-2-oxazolidinone, a compound of claim 1.
5. 5-methyl-5-(4-methoxy-3-propoxyphenyl)-2-oxazolidinone, a compound of claim 1.
6. 5-methyl-5-(3-butoxy-4-methoxyphenyl)-2-oxazolidinone, a compound of claim 1.
7. 5-methyl-5-(3-isopropoxy-4-methoxyphenyl)-2-oxazolidinone, a compound of claim 1.
8. 5-methyl-5-(3-ethoxy-4-methoxyphenyl)-2-oxazolidinone, a compound of claim 1.
9. 5-methyl-5-(3-cyclopentyloxy-4-methoxyphenyl)-2-oxazolidinone.
10. An optical antipode of a compound of claim 1.
11. An optical antipode of a compound of claim 5.
12. An optical antipode of a compound of claim 8.
13. An optical antipode of a compound of claim 9.
14. A pharmaceutical preparation comprising an effective amount of one or two oxazolidinone derivatives according to claim 1, and a pharmaceutically acceptable carrier.

* * * * *